(12) United States Patent
Mukhopadhyay et al.

(10) Patent No.: US 7,132,578 B1
(45) Date of Patent: Nov. 7, 2006

(54) ONE-STEP SYNTHESIS OF CF₃-1

(75) Inventors: Sudip Mukhopadhyay, Buffalo, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 83 days.

(21) Appl. No.: 11/181,311

(22) Filed: Jul. 14, 2005

(51) Int. Cl.
*C07C 17/00* (2006.01)

(52) U.S. Cl. ............ 570/174; 570/101; 570/123; 570/162; 570/246; 570/247

(58) Field of Classification Search ........... 570/101, 570/123, 162, 174, 247, 254
See application file for complete search history.

(56) References Cited

U.S. PATENT DOCUMENTS 6,977,316 B1 * 12/2005 Mukhopadhyay et al. .. 570/174

FOREIGN PATENT DOCUMENTS

| | | |
|---|---|---|
| DE | 1805457 | 10/1998 |
| EP | 0266281 A1 | 9/1987 |
| JP | 52-68110 | 6/1977 |

OTHER PUBLICATIONS

Nagasaki, Noritaka et al., *Study on a Novel Catalytic Reaction and Its Mechanism for CF3I Synthesis*, Catalysis Today (2004), 88(3-4), 121-126 (abstract only).

Lee, KH, et al., *Synthesis of CF3I by Direct Iodination of CF3COOH on Solid Catalyst*, Waste Research Team, Hwahak Konghak, (2001) 39(2), 144-149 (abstract only).

Su, D., et al., *A Simple, Novel Method for the Preparation of Trifluoromethyl Iodide and Diiodoifluoromethane*, Journal of the Chemical Society, Chemical Communications (1992) (11) 807-808 (abstract only).

Naumann et al., *Preparation and Properties of ZnBr(CF3)2L—A Convenient Route for the Preparation of CF3I*, Journal of Fluoride Chemistry, 67 (1994) 91-93 (article enclosed).

* cited by examiner

*Primary Examiner*—Samuel Barts
(74) *Attorney, Agent, or Firm*—Colleen D. Szuch

(57) ABSTRACT

A process for the preparation of trifluoromethyl iodide is provided. The process includes the step of contacting in a reactor a compound represented by the formula:

$$CF_3-W$$

and a compound represented by the formula:

$$IF_n$$

wherein W can be H, Br, Cl, COOH, COCl, COOCH₃, COOC₂H₅, COCH₃, COPh, CF₃, Si(CH₃)₃, SPh, SCH₃, SSCF₃, SSPh, SSCH₃, or SO₂Cl, wherein n is 1, 3, 5, or 7, and wherein the step of contacting is carried out, at a temperature, pressure and for a length of time sufficient to produce trifluoromethyl iodide. The contacting step can be carried out in the presence or absence of a catalyst and the contacting step can be carried out in the presence or absence of air.

37 Claims, No Drawings

ONE-STEP SYNTHESIS OF CF$_3$-1

BACKGROUND OF THE INVENTION

1. Field of the Invention

The present invention generally relates to a process for the preparation of trifluoromethyl iodide. More particularly, the present invention relates to a process for the preparation of trifluoromethyl iodide from CF$_3$—W and IF$_n$, wherein W is H, Br, Cl, COOH, COCl, COOCH$_3$, COOC$_2$H$_5$, COCH$_3$, COPh, CF$_3$, Si(CH$_3$)$_3$, SPh, SCH$_3$, SSCF$_3$, SSPh, SSCH$_3$, or SO$_2$Cl, and n is 1, 3, 5 or 7, wherein in process is carried out in the presence or absence of oxygen co-feed.

2. Description of the Prior Art

An article by Dhooge et al. in the Proceedings of the 4th Conference on Aerospace Materials, Processes, and Environmental Technology, pages 259–268 (2000), describes vapor phase production process for the preparation of CF$_3$I by the reaction between CHF$_3$ with I$_2$ in the presence of a catalyst including alkali metal salts supported on an activated carbon carrier. The mechanism of the reaction appears to proceeds via :CF$_2$ (difluoro carbene) intermediates that are formed on the catalyst surface, followed by carbene disproportionation to •CF$_3$ radicals, followed by reaction with 12 to give CF$_3$I (see Nagasaki, Noritaka et al., Catalysis Today (2004), 88(3–4), 121–126).

JP 52068110 (1977) describes the preparation of CF$_3$I by vapor-phase reaction of Freon 23 with iodine in the presence of alkali or alkaline earth metal salts.

DE 1805457 (1970) describes the preparation of CF$_3$I and C$_2$F$_5$I from the reaction of corresponding bromides and KI without solvent.

Naumann et al., J. Fluorine Chem., 67(1), 91–3 (1994) describes the preparation of CF$_3$I from CF$_3$Br by a multi-step reaction, which employs elemental Zn.

European Patent Application EP 266,281 A1 (1988) describes the preparation of CF$_3$I from CF$_3$Br by contact with a metal or an alkali metal dithionite and SO$_2$ followed by treatment with iodine in a carboxylic or sulfonic acid.

Lee, K.-H. et al., Hwahak Konghak, 39(2), 144–149 (2001) describes the preparation of CF$_3$I by iodination of CF$_3$CO$_2$H with iodine using a flow reactor over various salt-impregnated catalysts.

Su, D. et al., J. Chem. Soc., Chem. Commun., (11), 807–8 (1992) describes the preparation of CF$_3$I by treatment of XCF$_2$CO$_2$Me (X=Cl or Br) with iodine in the presence of potassium fluoride and copper (I) iodide.

Chiriac, M. et al., Inst. Tehnol. Izot. Mol., 33(11), 1018–20 (1982) describes the preparation of CF$_3$I from AgO$_2$CCF$_3$ (silver trifluoroacetate).

However, in view of the high cost of the raw materials required and the formation of undesirable solid by-products that are difficult to dispose of, and because of the adverse impact of the solid by-products on the environment, none of the above described methods provide a practical and economical process that can be adapted to large scale production of high purity CF$_3$I. In addition, there are no reports in the literature of any catalytic vapor-phase process for making CF$_3$I in high yield. Accordingly, the discovery of a high yield, catalytic vapor-phase process, which avoids the formation of solid by-products and the adverse impact of such solid by-products on the environment would be welcome by the Chemical Industry.

These problems can be avoided by the use of a process for the preparation of trifluoromethyl iodide from CF$_3$—W and IF$_n$, wherein W is H, Br, Cl, COOH, COCl, COOCH$_3$, COOC$_2$H$_5$, COCH$_3$, COPh, CF$_3$, Si(CH$_3$)$_3$, SPh, SCH$_3$, SSCF$_3$, SSPh, SSCH$_3$, or SO$_2$Cl, and n is 1, 3, 5, or 7.

The present invention provides such a high yield, catalytic vapor-phase process, which avoids the formation of solid by-products and the adverse impact of such solid by-products on the environment.

SUMMARY OF THE INVENTION

In broad concept, the present invention provides a process for the preparation of trifluoromethyl iodide.

The process includes the step of:

contacting in a reactor a compound represented by the formula:

CF$_3$—W and a compound represented by the formula:

IF$_n$ wherein W is selected from is H, Br, Cl, COOH, COCl, COOCH$_3$, COOC$_2$H$_5$, COCH$_3$, COPh, CF$_3$, Si(CH$_3$)$_3$, SPh, SCH$_3$, SSCF$_3$, SSPh, SSCH$_3$, or SO$_2$Cl, wherein n is 1, 3, 5, or 7, and wherein the step of contacting is carried out at a temperature, pressure and for a length of time sufficient to produce trifluoromethyl iodide.

The present invention has the advantage of providing high yields and high purity trifluoromethyl iodide while avoiding the formation of solid by-products and their adverse impact on the environment.

These and other benefits of the present process will become more evident from the detailed description of the invention that follows.

DETAILED DESCRIPTION OF THE INVENTION

The present invention provides a process for the preparation of trifluoromethyl iodide from CF$_3$—W and IF$_n$ wherein W is H, Br, Cl, COOH, COCl, COOCH$_3$, COOC$_2$H$_5$, COCH$_3$, COPh, CF$_3$, Si(CH$_3$)$_3$, SPh, SCH$_3$, SSCF$_3$, SSPh, SSCH$_3$, or SO$_2$Cl and n is 1, 3, 5, 7.

CF$_3$I is a non-toxic, nonflammable compound, having a low global warming potential and an almost zero ozone depletion potential (See, for example, Dhooge et al., Proceedings of the 4th Conference on Aerospace Materials, Processes, and Environmental Technology, page 259–268 (2000)).

Further, the life cycle of the CF$_3$I in the atmosphere is only about two days. Therefore, the Chemical Industry has a substantial incentive to produce this compound by a low-cost and environmentally acceptable route for use as a refrigerant either alone or in combination with other existing refrigerants.

The present invention provides a catalytic process, which uses low cost feedstocks, such as, CHF$_3$ and Iodine-Fluorine complexes (IF$_n$) as the starting materials to produce CF$_3$I with high selectivity.

As mentioned herein above, the processes described in the prior art generally are limited to lab-scale demonstration. In addition, the raw materials used in these methods are either not readily available or are expensive. Therefore, a substantial incentive exists for the development of alternative commercial processes for the manufacture of CF$_3$I.

To achieve this objective, the present invention provides a process, which is catalytic and is commercially useful.

In broad concept, the present invention provides a process for preparing CF$_3$—I from CF$_3$—W and IF$_n$ wherein W is H, Br, Cl, COOH, COCl, COOCH$_3$, COOC$_2$H$_5$, COCH$_3$, COPh, CF$_3$, Si(CH$_3$)$_3$, SPh, SCH$_3$, SSCF$_3$, SSPh, SSCH$_3$, or SO$_2$Cl, and wherein n is 1, 3, 5, or 7.

While the chemical reactions that occur in this process are multistep and complex reactions, the initial step of the chemical reaction can be described by the following equation:

$$CF_3-W + IF_n \rightarrow CF_3-I + [F-W] + [F_{n-1}]$$

wherein F—W and $F_{n-1}$, being highly reactive compounds, can undergo further multistep and complex reactions to produce a variety of by-products the nature of which depends on the presence or absence of oxygen and the nature, presence or absence of a catalyst and/or other materials.

Preferred Embodiments

In a one preferred embodiment, W is hydrogen and $IF_n$ is IF (1a and 1b), wherein the process proceeds at least in part according to the following equation:

$$CF_3-H + IF \xrightarrow{Catalyst} CF_3-I + HF \quad (1a)$$

or at least in part according to the following equation:

$$2CF_3-H + IF + 1/2O_2 \xrightarrow{Catalyst} CF_3-I + CF_4 + H_2O \quad (1b)$$

In another preferred embodiment, W is bromine and $IF_n$ iodine monofluoride (IF), wherein the process proceeds according to the following equation:

$$CF_3-Br + IF \xrightarrow{Catalyst} CF_3-I + BrF \quad (2)$$

In still another preferred embodiment, W is chlorine and $IF_n$ iodine monofluoride (IF), wherein the process proceeds according to the following equation:

$$CF_3-Cl + IF \xrightarrow{Catalyst} CF_3-I + ClF \quad (3)$$

In yet another preferred embodiment, W is COOH and $IF_n$ iodine monofluoride (IF), wherein the process proceeds according to the following equation:

$$CF_3-COOH + IF \xrightarrow{Catalyst} CF_3-I + CO_2 + HF \quad (4)$$

In still another embodiment, W is COCl and $IF_n$ is iodine monofluoride (IF), wherein the process proceeds at least in part according to the following equation:

$$CF_3-COCl + IF \xrightarrow{Catalyst} CF_3-I + CO + ClF \quad (5)$$

or according to the following equation:

$$CF_3-COOCH_3 + IF \xrightarrow{Catalyst} CF_3-I + FCOOCH_3 \quad (6a)$$

$$CF_3-COOC_2H_5 + IF \longrightarrow CF_3-I + FCOOC_2H_5 \quad (6b)$$

In yet another embodiment, W is $COCH_3$ or COPh, $IF_n$ is IF, and the process proceeds with or without $O_2$ at least in part according to the following equation:

$$CF_3-COCH_3 + IF \xrightarrow{Catalyst} CF_3-I + CH_3COF \quad (7a)$$

$$CF_3-COPh + IF \longrightarrow CF_3-I + PhCOF \quad (7b)$$

In still another embodiment, W is $CF_3$ and $IF_n$ is IF, wherein the process proceeds, with or without $O_2$, at least in part according to the following equation:

$$CF_3-CF_3 + IF \rightarrow CF_3-I + CF_4 \quad (8)$$

In still a further embodiment, W is $Si(CH_3)_3$ and $IF_n$ is IF (9), wherein the process proceeds, at least in part according to the following equation:

$$CF_3-Si(CH_3)_3 + IF \rightarrow CF_3-I + F-Si(CH_3)_3 \quad (9)$$

In still a further embodiment, W is SPh or $SCH_3$ and $IF_n$ is IF, wherein the process proceeds, at least in part according to the following equation:

$$CF_3-SPh + IF \rightarrow CF_3-I + PhSF \quad (10a)$$

$$CF_3-SCH_3 + IF \rightarrow CF_3-I + CH_3SF \quad (10b)$$

In still another embodiment, W is $SSCF_3$ or SSPh or $SSCH_3$ and $IF_n$ is IF, wherein the process proceeds, with or without $O_2$, at least in part according to the following equation:

$$CF_3-S-S-CF_3 + IF + 2O_2 \rightarrow CF_3-I + CF_4 + 2SO_2 \quad (11a)$$

$$CF_3-S-S-CF_3 + IF + 2O_2 \rightarrow CF_3-I + CF_4 + 2SO_2 \quad (11b)$$

$$CF_3-S-S-CF_3 + IF + 2O_2 \rightarrow CF_3-I + CF_4 + 2SO_2 \quad (11c)$$

In yet another preferred embodiment, W is $SO_2Cl$ and $IF_n$ is iodine monofluoride (IF), wherein the process proceeds according to the following equation:

$$CF_3-SO_2Cl + IF \rightarrow CF_3-I + SO_2 + ClF \quad (12)$$

In still another embodiment, W is H, Br, Cl, COOH, COCl, $COOCH_3$, $COOC_2H_5$, $COCH_3$, COPh, $CF_3$, $Si(CH_3)_3$, SPh, $SCH_3$, $SSCF_3$, SSPh, $SSCH_3$, or $SO_2Cl$ and $IF_n$ is $IF_3$, wherein the process proceeds, with or without $O_2$, at least in part according to the following equation:

$$CF_3-W + IF_3 \rightarrow CF_3-I + WF + F_2 \quad (13)$$

In still another embodiment, W is H, Br, Cl, COOH, COCl, $COOCH_3$, $COOC_2H_5$, $COCH_3$, COPh, $CF_3$, $Si(CH_3)$ $_3$, SPh, SCH$_3$, SSCF$_3$, SSPh, SSCH$_3$, or SO$_2$Cl and IF$_n$ is IF$_5$, wherein the process proceeds, with or without O$_2$, at least in part according to the following equation:

$$CF_3—W+IF_5 \rightarrow CF_3—I+WF+2F_2 \quad (14)$$

In still another embodiment, W is H, Br, Cl, COOH, COCl, COOCH$_3$, COOC$_2$H$_5$, COCH$_3$, COPh, CF$_3$, Si(CH$_3$)$_3$, SPh, SCH$_3$, SSCF$_3$, SSPh, SSCH$_3$, or SO$_2$Cl and IF$_n$ is IF$_7$, wherein the process proceeds, with or without O$_2$, at least in part according to the following equation:

$$CF_3—W+IF_7 \rightarrow CF_3—I+WF+3F_2 \quad (15)$$

As mentioned herein above, being highly reactive compounds, the F—W and F$_{n-1}$ can undergo further multi-step and complex reactions to produce a variety of by-products the nature of which depends on the presence or absence of oxygen and the nature, presence or absence of a catalyst and/or other materials.

Process Conditions:

In the practice of the process of the present invention, the step of contacting is preferably carried out at a temperature from about 20° C. to about 650° C., at a pressure from about 1 atm to about 100 atm, and for a length of time from about 0.01 sec to about 300 hours.

The process can be either a batch process or it can be a continuous process.

The reactor can further comprise a diluent, such as, a gas, a solvent or a mixture thereof. The diluent can be gas or a liquid.

When the diluent is a gas, the diluent can be nitrogen, helium, argon or a mixture thereof. When the diluent is a liquid, the diluent is preferably a solvent, such as, a liquid fluorocarbon.

The process can further include one or more of the following steps:

(1) passing the trifluoromethyl iodide through a scrubber containing an aqueous alkali solution;

(2) passing the trifluoromethyl iodide through a scrubber containing an drying agent;

(3) cooling at a temperature below the boiling temperature of the trifluoromethyl iodide to condense; and (4) isolating the trifluoromethyl iodide from the reaction mixture in substantially pure form.

In operation, preferably at least 10 wt % of the reactants are converted to trifluoromethyl iodide. More preferably, at least 80 wt % of the reactants are converted to trifluoromethyl iodide, and most preferably, at least 95 wt % of the reactants are converted to trifluoromethyl iodide.

The following non-limiting examples are illustrative of the various embodiments of the present invention. It is within the ability of a person of ordinary skill in the art to select other variable from among the many known in the art without departing from the scope of the present invention. Accordingly, these examples shall serve to further illustrate the present invention, not to limit them.

Unless otherwise indicated, all parts and percentages are on a weight basis.

EXAMPLE 1

One-step synthesis of CF$_3$I from CHF$_3$

CF$_3$I is synthesized in a cost-effective way by reacting CHF$_3$ with IF and O$_2$ (or Air) in the presence of a catalyst including one or more iodide, nitrate, oxide, bromide, carbonate, chloride, acetate, acetylacetonate salts of Cs, K, Rb, Cu (II), Hg (II), Pt (II), Pd (II), Co (III), Mn (III), Rh (III), Ni (II), V (IV), Tl (III), and Ge (III) at 50–600° C. in a vapor or liquid-phase process.

The catalyst salts can be used directly (100 wt %) or a portion (2–60 wt %) on an active support such as activated carbon, alumina, SiO$_2$, or ZrO$_2$. A mixture of salts supported on an active carbon, alumina, glass, SiO$_2$, SBA-15 support can also be used to obtain higher selectivity to CF$_3$I formation.

Iodine fluoride is available from Honeywell International, Inc. It can also be prepared from iodine and fluorine according to the procedure described by S. Rozen et al., *J. Org. Chem.*, 53(5), 1123 (1988).

20 SCCM (Standard Cubic Centimeter Per Minute) of CHF$_3$ and 20 SCCM of IF are passed through a 50 cc 10 wt % CsNO$_3$, 3 wt % RbNO$_3$ and 1 wt % KNO$_3$ supported on activated carbon in a ½-inch reactor (Monel) in the presence or absence of 20 SCCM of air or O$_2$ at 550° C. to yield 40–95 mol % of CF$_3$I. The product mixture was analyzed by GC and GCMS.

The reaction proceeds well without Oxygen, however, the presence of Oxygen helps to increase the catalyst life by burning out any coke formed during the reaction.

CHF$_3$, which is a common byproduct from fluorocarbon industries, can also be synthesized easily by vapor phase reaction of HF with CHCl$_3$ in the presence of a chromium oxide based catalyst at 200–450° C. Thus, the overall process is highly cost effective.

EXAMPLE 2

Preparation of CF$_3$I from CF$_3$Br or CF$_3$Cl, and IF

CF$_3$I is synthesized in a cost-effective way by reacting 50 SCCM of CF$_3$Br or CF$_3$Cl with 50 SCCM of IF in the presence of 100 cc 5 wt % Pd/C catalyst at 50–600° C. in a vapor phase process. The conversion was 30% and the selectivity to CF$_3$I was 70%.

In a liquid phase process 10 g of CF$_3$Br was reacted with 20 g IF in 100 ml DMF and DMSO as the solvent in the presence of 2 g of 3 wt % Pd/C catalyst at 100° C. in the presence of 2 atm of H$_2$. The same reaction was also performed in the presence of Zn as the reducing agent. The yield was 20–45%.

EXAMPLE 3

Preparation of CF$_3$I from CF$_3$COOH, CF$_3$COCl, CF$_3$COOCH$_3$, CF$_3$COOC$_2$H$_5$, CF$_3$COCH$_3$, CF$_3$COPh, CF$_3$CF$_3$, CF$_3$Si(CH$_3$)$_3$, or CF$_3$SO$_3$Cl, and IF CF$_3$I is synthesized in a cost-effective way by reacting each one of those starting materials (50 SCCM) with 100 SCCM of IF in the presence of 100 cc 5 wt % Pd/C, Cu/C and Pt/C catalyst at 250–550° C. in a vapor phase process. The conversion was 43% and the selectivity to CF$_3$I was 92%.

In a liquid phase process, 10 g of any one of those reactants was heated with 20 g IF in the presence of 25 ml of 30 wt % H$_2$O$_2$. VO(AcAc)$_2$ was used as the solvent. The yield was 15–54%.

EXAMPLE 4

Preparation of CF$_3$I from CF$_3$—SPh, CF$_3$—SCH$_3$, CF$_3$—SS—CF$_3$, CF$_3$—SS—Ph, or CF$_3$—SS—CH$_3$, and IF CF$_3$I is synthesized by reacting each one of those starting materials (100 SCCM) with 250 SCCM of IF in the presence of 100 cc 20 wt % CsNO$_3$ on carbon catalyst at 350–750° C. in a vapor phase process in the presence or absence of 30 SCCM of air. The conversion was 60% and the selectivity to CF$_3$I was 72%.

In a liquid phase process, 10 g of any one of those reactants was heated with 20 g IF in the presence of 25 ml of 30 wt % $H_2O_2$. $VO(AcAc)_2$ was used as the solvent. The yield was 40–60%.

Preparation of $CF_3I$ from $CF_3$—S—Ph, $CF_3$—S—$CH_3$, $CF_3$—S—S—$CF_3$, $CF_3$—S—S—Ph, $CF_3$—S—S—$CH_3$, and $IF_3$ $CF_3I$ is synthesized by reacting each one of the above sulfide and disulfide starting materials (100 SCCM) with of $IF_3$(150 SCCM), available from Honeywell International, Inc., Morristown, N.J., USA in the presence of 100 cc 20 wt % $CsNO_3$ on carbon catalyst at 350–750° C. in a vapor phase process in the presence or absence of 30 SCCM of air.

The conversion was about 50% and the selectivity to $CF_3I$ was about 42%.

In a liquid phase process, 10 g of any one of the above sulfide and disulfide reactants was heated with 20 g $IF_3$ in the presence of 25 ml of 30 wt % $H_2O_2$. $VO(AcAc)_2$ was used as the solvent. The yield was about 30–40%.

Preparation of $CF_3I$ from $CF_3$—S—Ph, $CF_3$—S—$CH_3$, $CF_3$—S—S—$CF_3$, $CF_3$—S—S—Ph, $CF_3$—S—S—$CH_3$, and $IF_5$ Iodine pentafluoride is available from Honeywell International, Inc. Iodine pentafluoride can also be prepared from iodine oxides, alkali metal iodates, or alkaline earth iodates with an excess of $SF_4$ according to a procedure described U.S. Pat. No. 2,904,403 to Wm. C. Smith, E. I. du Pont de Nemours & Co., (1959) as follows:

$IF_5$ is prepared by reaction of iodine oxides, alkali metal iodates, or alkaline earth iodates with an excess of $SF_4$ under anhydrous conditions at 50–250° C. at atmospheric pressure or above. Air and oxygen are excluded. Thus, a bomb lined with stainless steel is charged with 33.4 g of $I_2O_5$, cooled in a solid $CO_2$-acetone bath, and evacuated down to 1 mm. It is then charged with 66 g of $SF_4$, sealed, and heated at 60° C. for 4 hrs and at 120° C. for 10 hrs. After cooling, 44.0 g of crude $IF_5$ was removed and distilled to yield 27.9 g. of pure product, bp 102–110° C. Similarly, $KIO_3$ was reacted with $SF_4$ to yield $IF_5$ and $KIF_6$.

$CF_3I$ is synthesized by reacting each one of the above sufide or disulfide starting materials (100 SCCM) with 250 SCCM of $IF_5$ in the presence of 100 cc 20 wt % $CsNO_3$ on carbon catalyst at 350–750° C. in a vapor phase process in the presence or absence of 30 SCCM of air.

The conversion was about 50% and the selectivity to $CF_3I$ was about 42%.

In a liquid phase process, 10 g of any one of the above sulfide and disulfide reactants was heated with 20 g $IF_5$ in the presence of 25 ml of 30 wt % $H_2O_2$. $VO(AcAc)_2$ was used as the solvent. The yield was 30–40%.

Preparation of $CF_3I$ from $CF_3$—S—Ph, $CF_3$—S—$CH_3$, $CF_3$—S—S—$CF_3$, $CF_3$—S—S—Ph, $CF_3$—S—S—$CH_3$, and $IF_7$ $CF_3I$ is synthesized by reacting each one of the above sulfide and disulfide starting materials 100 SCCM with 120 SCCM of $IF_7$, available from Honeywell International, Inc., Morristown, N.J., USA in the presence of 100 cc 20 wt % $CsNO_3$ on carbon catalyst at 350–750° C. in a vapor phase process in the presence or absence of 30 SCCM of air.

The conversion was about 50% and the selectivity to $CF_3I$ was about 42%.

In a liquid phase process, 10 g of any one of the above sulfide and disulfide reactants was heated with 20 g $IF_7$ in the presence of 25 ml of 30 wt % $H_2O_2$. $VO(AcAc)_2$ was used as the solvent. The yield was about 30–40%.

The present invention has been described with particular reference to the preferred embodiments. It should be understood that variations and modifications thereof can be devised by those skilled in the art without departing from the spirit and scope of the present invention. Accordingly, the present invention embraces all such alternatives, modifications and variations that fall within the scope of the appended claims.

What is claimed is:

1. A process for the preparation of trifluoromethyl iodide, comprising the step of:

contacting in a reactor a compound represented by the formula:

$CF_3$—W and a compound represented by the formula:

$IF_n$ wherein W is selected from the group consisting of: H, Br, Cl, COOH, COCl, $COOCH_3$, $COOC_2H_5$, $COCH_3$, COPh, $CF_3$, $Si(CH_3)_3$, SPh, $SCH_3$, $SSCF_3$, SSPh, $SSCH_3$, and $SO_2Cl$;

wherein n is 1, 3, 5, or 7; and wherein the step of contacting is carried out, at a temperature, pressure and for a length of time sufficient to produce trifluoromethyl iodide.

2. The process of claim 1, wherein the contacting step is carried out in the presence of a catalyst.

3. The process of claim 1, wherein the contacting step is carried out in the absence of a catalyst.

4. The process of claim 1, wherein the contacting step is carried out in the presence of air.

5. The process of claim 1, wherein the contacting step is carried out in the absence of air.

6. The process of claim 1, wherein said step of contacting is carried out at a temperature from about 20° C. to about 650° C.

7. The process of claim 1, wherein said step of contacting is carried out at a pressure from about 1 atm to about 100 atm.

8. The process of claim 1, wherein said step of contacting is carried out for a length of time from about 0.01 sec to about 300 hours.

9. The process of claim 1, wherein the process proceeds at least in part according to the following equation:

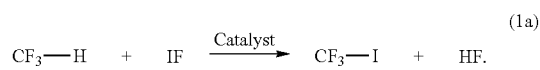
(1a)

10. The process of claim 1, wherein the process proceeds at least in part according to the following equation:

(1b)

11. The process of claim 1, wherein the process proceeds according to the following equation:

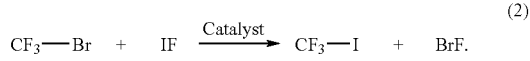
(2)

12. The process of claim 1, wherein the process proceeds according to the following equation:

$$CF_3-Cl + IF \xrightarrow{Catalyst} CF_3-I + ClF. \quad (3)$$

13. The process of claim 1, wherein the process proceeds according to the following equation:

$$CF_3-COOH + IF \xrightarrow{Catalyst} CF_3-I + CO_2 + HF. \quad (4)$$

14. The process of claim 1, wherein the process proceeds at least in part according to the following equation:

$$CF_3-COCl + IF \xrightarrow{Catalyst} CF_3-I + CO + ClF. \quad (5)$$

15. The process of claim 1, wherein the process proceeds at least in part according to the following equation:

$$CF_3-COOCH_3 + IF \xrightarrow{Catalyst} CF_3-I + FCOOCH_3. \quad (6a)$$

16. The process of claim 1, wherein the process proceeds at least in part according to the following equation:

$$CF_3-COOC_2H_5 + IF \rightarrow CF_3-I + FCOOC_2H_5 \quad (6b).$$

17. The process of claim 1, wherein W is $COCH_3$ or $COPh$, $IF_n$ is IF, and the process proceeds, with or without $O_2$, at least in part according to the following equations:

$$CF_3-COCH_3 + IF \xrightarrow{Catalyst} CF_3-I + CH_3COF \quad (7a)$$

$$CF_3-COPh + IF \rightarrow CF_3-I + PhCOF. \quad (7b)$$

18. The process of claim 1, wherein W is $CF_3$ and $IF_n$ is IF, and the process proceeds at least in part according to the following equation:

$$CF_3-CF_3 + IF \rightarrow CF_3-I + CF_4 \quad (8).$$

19. The process of claim 1, wherein W is $Si(CH_3)_3$ and $IF_n$ is IF, and the process proceeds at least in part according to the following equation:

$$CF_3-Si(CH_3)_3 + IF \rightarrow CF_3-I + F-Si(CH_3)_3 \quad (9).$$

20. The process of claim 1, wherein W is SPh or $SCH_3$ and $IF_n$ is IF, and the process proceeds at least in part according to the following equations:

$$CF_3-SPh + IF \rightarrow CF_3-I + PhSF \quad (10a)$$

$$CF_3-SCH_3 + IF \rightarrow CF_3-I + CH_3SF \quad (10b).$$

21. The process of claim 1, wherein W is $SSCF_3$ or SSPh or $SSCH_3$ and $IF_n$ is IF, and the process proceeds, with or without $O_2$, at least in part according to the following equations:

$$CF_3-S-S-CF_3 + IF + 2O_2 \rightarrow CF_3-I + CF_4 + 2SO_2 \quad (11a)$$

$$CF_3-S-S-CF_3 + IF + 2O_2 \rightarrow CF_3-I + CF_4 + 2SO_2 \quad (11b)$$

$$CF_3-S-S-CF_3 + IF + 2O_2 \rightarrow CF_3-I + CF_4 + 2SO_2 \quad (11c).$$

22. The process of claim 1, wherein W is $SO_2Cl$ and $IF_n$ is iodine monofluoride, and the process proceeds at least in part according to the following equation:

$$CF_3-SO_2Cl + IF \rightarrow CF_3-I + SO_2 + ClF \quad (12).$$

23. The process of claim 1, wherein W is H, Br, Cl, COOH, COCl, $COOCH_3$, $COOC_2H_5$, $COCH_3$, COPh, $CF_3$, $Si(CH_3)_3$, SPh, $SCH_3$, $SSCF_3$, SSPh, $SSCH_3$, or $SO_2Cl$ and $IF_n$ is $IF_3$, wherein the process proceeds, with or without $O_2$, at least in part according to the following equation:

$$CF_3-W + IF_3 \rightarrow CF_3-I + WF + F_2 \quad (13).$$

24. The process of claim 1, wherein W is H, Br, Cl, COOH, COCl, $COOCH_3$, $COOC_2H_5$, $COCH_3$, COPh, $CF_3$, $Si(CH_3)_3$, SPh, $SCH_3$, $SSCF_3$, SSPh, $SSCH_3$, or $SO_2Cl$ and $IF_n$ is $IF_5$, wherein the process proceeds, with or without $O_2$, at least in part according to the following equation:

$$CF_3-W + IF_5 \rightarrow CF_3-I + WF + 2F_2 \quad (14).$$

25. The process of claim 1, wherein W is H, Br, Cl, COOH, COCl, $COOCH_3$, $COOC_2H_5$, $COCH_3$, COPh, $CF_3$, $Si(CH_3)_3$, SPh, $SCH_3$, $SSCF_3$, SSPh, $SSCH_3$, or $SO_2Cl$ and $IF_n$ is $IF_7$, wherein the process proceeds, with or without $O_2$, at least in part according to the following equation:

$$CF_3-W + IF_7 \rightarrow CF_3-I + WF + 3F_2 \quad (15).$$

26. The process of claim 1, wherein the process is a batch process.

27. The process of claim 1, wherein the process is a continuous process.

28. The process of claim 1, wherein the reactor further comprises a diluent selected from the group consisting of a gas, a solvent and a mixture thereof.

29. The process of claim 28, wherein said gas is selected from the group consisting of: nitrogen, helium, argon and a mixture thereof.

30. The process of claim 28, wherein said solvent is a liquid fluorocarbon.

31. The process of claim 1, further comprising the step of: passing the trifluoromethyl iodide through a scrubber containing an aqueous alkali solution.

32. The process of claim 1, further comprising the step of: passing the trifluoromethyl iodide through a scrubber containing a drying agent.

33. The process of claim 1, further comprising the step of: cooling at a temperature below the boiling temperature of the trifluoromethyl iodide to condense.

34. The process of claim 1, further omprising the step of: isolating the trifluoromethyl iodide from the reaction mixture in substantially pure form.

35. The process of claim 1, wherein at least 10 wt % of the reactants are converted to trifluoromethyl iodide.

36. The process of claim 1, wherein at least 80 wt % of the reactants are converted to trifluoromethyl iodide.

37. The process of claim 1, wherein at least 95 wt % of the reactants are converted to trifluoromethyl iodide.

* * * * *